United States Patent
Kim et al.

(10) Patent No.: US 10,456,085 B2
(45) Date of Patent: Oct. 29, 2019

(54) METHOD AND DEVICE FOR MEASURING A BIOLOGICAL SIGNAL

(71) Applicants: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

(72) Inventors: Sangkyu Kim, Yongin-si (KR); Jungmok Bae, Seoul (KR); Joonhyung Lee, Yongin-si (KR); Hyeseon Lee, Pohang-si (KR); Hoeil Chung, Seoul (KR); Junghye Lee, Ulsan (KR); Kyeol Chang, Seoul (KR); Seongho Cho, Gwacheon-si (KR)

(73) Assignees: SAMSUNG ELECTRONICS CO., LTD., Suwon-si (KR); IUCF-HYU (INDUSTRY-UNIVERSITY COOPERATION FOUNDATION HANYANG UNIVERSITY), Seongdong-Gu, Seoul (KR)

( * ) Notice: Subject to any disclaimer, the term of this patent is extended or adjusted under 35 U.S.C. 154(b) by 839 days.

(21) Appl. No.: 15/042,899

(22) Filed: Feb. 12, 2016

(65) Prior Publication Data

US 2016/0235375 A1     Aug. 18, 2016

(30) Foreign Application Priority Data

Feb. 13, 2015 (KR) .......... 10-2015-0022721

(51) Int. Cl.
*A61B 5/00* (2006.01)
*G16H 40/63* (2018.01)

(52) U.S. Cl.
CPC .......... *A61B 5/7275* (2013.01); *A61B 5/0075* (2013.01); *A61B 5/7246* (2013.01); *G16H 40/63* (2018.01)

(58) Field of Classification Search
CPC ... A61B 5/7275; A61B 5/0075; A61B 5/7246; G06F 19/00
See application file for complete search history.

(56) References Cited

U.S. PATENT DOCUMENTS

2007/0005257 A1   1/2007   Cheng et al.
2008/0084487 A1   4/2008   Yoshida
(Continued)

FOREIGN PATENT DOCUMENTS

JP   2007-113743 A   5/2007
JP   2008-098818 A   4/2008
(Continued)

*Primary Examiner* — Joel Lamprecht
(74) *Attorney, Agent, or Firm* — Sughrue Mion, PLLC

(57) ABSTRACT

A method and device for measuring a biological variable are provided. The method of measuring the biological variable may include detecting an infrared signal which is irradiated toward a body part and is reflected therefrom, extracting spectrum data from the detected infrared signal, obtaining intensity data corresponding to a preset frequency from the extracted spectrum data, obtaining a biological information-measuring model by performing multiple linear regression (MLR) on the obtained data, and measuring a biological signal of the body part by using the obtained biological information-measuring model.

14 Claims, 6 Drawing Sheets

(56) References Cited

U.S. PATENT DOCUMENTS

| | | | |
|---|---|---|---|
| 2014/0275854 A1* | 9/2014 | Venkatraman | A61B 5/721 |
| | | | 600/301 |
| 2014/0378810 A1* | 12/2014 | Davis | G06F 16/245 |
| | | | 600/407 |

FOREIGN PATENT DOCUMENTS

| | | |
|---|---|---|
| KR | 10-2014-0002150 A | 1/2014 |
| WO | 2008086596 A1 | 7/2008 |

\* cited by examiner $$[DAT_k] = \begin{bmatrix} 1 & X_{11} & \bullet & \bullet & X_{1k} \\ 1 & X_{21} & \bullet & \bullet & X_{2k} \\ \bullet & & & & \bullet \\ \bullet & & & & \bullet \\ \bullet & & & & \bullet \\ 1 & X_{n1} & \bullet & \bullet & X_{nk} \end{bmatrix}$$

```
IAMB(T)
/* add true positives to MB */
1    MB = 0
2    repeat
3        Y = atg:max_{x∈(U\MB\(T)} dep(T,X|MB)
4        if T ⊥ Y|MB then
5    MB = MB ∪ {Y}
6    until MB does not change
/* remove false positives from MB */
7    for each  X ∈ MB do
8    if  T ⊥ Y|(MB\{X}) then
9        MB = MB\{X}
10   return  MB
```

METHOD AND DEVICE FOR MEASURING A BIOLOGICAL SIGNAL

CROSS-REFERENCE TO RELATED APPLICATIONS

This application claims priority from Korean Patent Application No. 10-2015-0022721, filed on Feb. 13, 2015, in the Korean Intellectual Property Office, the disclosure of which is incorporated herein in its entirety by reference.

BACKGROUND

1. Field

The present disclosure relates to methods and devices for measuring a biological signal.

2. Description of the Related Art

A biological signal is generally measured by collecting blood by using an invasive method and performing a specific reaction between a reagent and a material in the blood. However, collecting blood by inserting a needle in a vein is painful. Furthermore, reagents used for respective biomolecules to be measured are different from each other. Therefore, cost increases as the number of biomolecules to be measured increases.

Alternatively, in a non-invasive method, light is used for measuring a biological signal. In the non-invasive method, intensity of light reflected after irradiating skin with light is measured, and a desired biological signal is measured by deriving information that is included in a spectrum of reflected light and is derived by measuring the light intensity. Biological tissue includes skin tissue, blood vessels, and blood, and thus, various complicated signals are included in a spectrum thereof. Therefore, an effective algorithm is required to extract information about a biological signal to be measured from a complicated and superimposed spectrum.

SUMMARY

Provided are methods and devices for measuring a biological signal. Further provided is a computer program that is executed via hardware and is stored in a medium to execute the method.

Additional aspects will be set forth in part in the description which follows and, in part, will be apparent from the description, or may be learned by practice of the presented exemplary embodiments.

According to an aspect of an exemplary embodiment, a method of measuring a biological signal includes detecting an infrared signal which is irradiated toward a body part and is reflected therefrom, extracting spectrum data from the detected infrared signal, obtaining data corresponding to a preset frequency from the extracted spectrum data, obtaining a biological information-measuring model by performing multiple linear regression (MLR) on the obtained data; and measuring a biological signal of the body part by using the obtained biological information-measuring model.

The extracting of the spectrum data may further include correcting the extracted spectrum data along a reference line.

The extracting of the spectrum data may further include correcting a basic value of the extracted spectrum data.

The obtaining of the data may include obtaining the data by using Incremental Association Markov Blanket (IAMB) algorithm from among Markov Blanket searching algorithms.

The obtaining of the data may include obtaining data corresponding to a frequency within a prescribed range including the preset frequency from the extracted spectrum data.

The obtaining of the data may include obtaining an average value of pieces of data corresponding to the frequency within a prescribed range, and the obtaining of the biological information-measuring model may include obtaining the biological information-measuring model by performing MLR on the obtained average value.

The obtaining of the data may include setting a prescribed range of each of the preset frequency, respectively.

The obtaining of the data may include obtaining data corresponding to a frequency input by a user, the frequency input including the preset frequency from the extracted spectrum data.

The measuring of the biological signal of the body part may measure the biological signal of the body part based on the data corresponding to the input frequency and the biological information-measuring model.

According to an aspect of another exemplary embodiment, a device for measuring a biological signal includes a detector configured to detect an infrared signal which is irradiated toward a body part and is reflected therefrom, an extractor configured to extract spectrum data from the detected infrared signal, a data obtainer configured to obtain data corresponding to a preset frequency from the extracted spectrum data, a model obtainer configured to obtain a biological information-measuring model by performing multiple linear regression (MLR) on the obtained data, and a biological signal measurer configured to measure a biological signal of the body part by using the obtained biological information-measuring model.

The data obtainer may obtain the data by using Incremental Association Markov Blanket (IAMB) algorithm from among Markov Blanket searching algorithms.

The data obtainer may further obtain data corresponding to a frequency within a prescribed range comprising the preset frequency from the extracted spectrum data.

The data obtainer may further obtain an average value of pieces of data corresponding to the frequency within a prescribed range, and the model obtainer may further obtain the biological information-measuring model by performing MLR on the obtained average value.

The data obtainer may further set a prescribed range of each of the preset frequency, respectively.

The extractor may further correct the extracted spectrum data along a reference line.

The extractor may further correct a basic value of the extracted spectrum data.

The data obtainer may further obtain data corresponding to a frequency input by a user, the frequency input comprising the preset frequency from the extracted spectrum data.

The biological signal measurer may further measure the biological signal of the body part based on the data corresponding to the input frequency and the biological information-measuring model.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
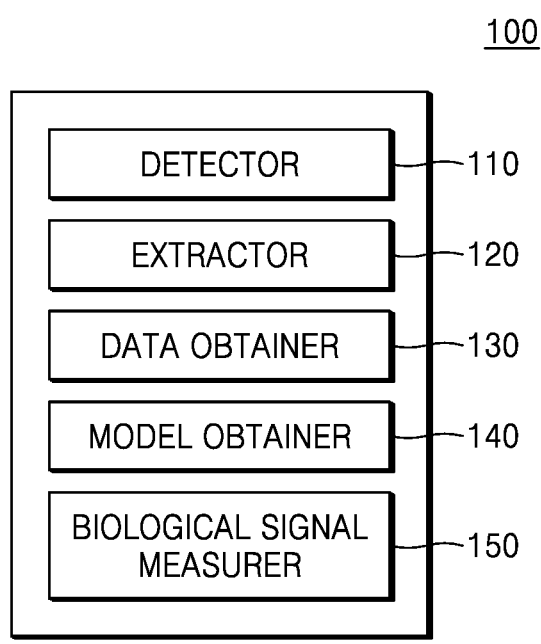
FIG. 1 is a configuration diagram of a device for measuring a biological signal according to an exemplary embodiment.

Reference will now be made in detail to exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain various aspects of the exemplary embodiments.

The terms used in the present specification will be briefly described, and the exemplary embodiments will be described in detail.

Hereinafter, the exemplary embodiments will be described more fully with reference to the accompanying drawings, in which the exemplary embodiments are shown. The exemplary embodiments may, however, be embodied in many different forms and should not be construed as limited to the embodiments set forth herein. Rather, these embodiments are provided so that this disclosure will be thorough and complete, and will fully convey the scope of the exemplary embodiments to one of ordinary skill in the art. Sizes of components in the drawings may be exaggerated for convenience of explanation. In other words, since sizes and thicknesses of components in the drawings are arbitrarily illustrated for convenience of explanation, the following embodiments are not limited thereto.

Throughout the specification, when a portion "includes" an element, another element may be further included, rather than excluding the existence of the other element, unless otherwise described. In addition, a term "unit" used in the specification indicates a software or hardware component such as field-programmable logic array (FPLA) and application-specific integrated circuit (ASIC), and the "unit" performs a particular function. However, the "unit" is not limited to software or hardware. The "unit" may be configured to be stored in an addressable storing medium or to play back one or more processors. Accordingly, the "unit" may include, for example, software components, object-oriented software components, components such as class components and task components, processors, formulas, attributes, procedures, subroutines, segments of program codes, drivers, firmware, micro codes, circuits, data, database, data structures, tables, arrays and variables. Functions provided in components and "units" may be combined into a smaller number of components and "units", or may be further divided into additional components and "units."

Below, a detailed description will be given about exemplary embodiments with reference to attached drawings such that one with an ordinary skill in the art may easily understand. In the description of the exemplary embodiments, certain detailed explanations of the related art are omitted when it is deemed that they may unnecessarily obscure the description of the exemplary embodiments.

FIG. 1 is a configuration diagram of a device 100 for measuring a biological signal according to an embodiment. The biological signal measuring device 100 may include a detector 110, an extractor 120, a data obtainer 130, a model obtainer 140, and a biological signal measurer 150.

The detector 110 may detect an infrared signal which is irradiated toward a body part and is reflected therefrom. The detector 110 may also detect an infrared signal which is irradiated toward a body part and is scattered therefrom.

The extractor 120 may extract spectrum data from the detected infrared signal. The extractor 120 may correct the extracted spectrum data along a reference line. The extractor 120 may correct a basic value of the extracted spectrum data.

The data obtainer 130 may obtain data corresponding to a preset frequency from the extracted spectrum data. Furthermore, the data obtainer 130 may obtain data by using an Incremental Association Markov Blanket (IAMB) algorithm from among Markov Blanket searching algorithms. The data obtainer 130 may obtain data corresponding to a frequency within a prescribed range including the preset frequency from the extracted spectrum data. For example, when the preset frequency is 100 MHz, the data obtainer 130 may obtain data corresponding to a frequency of 90 MHZ to 110 MHZ. Furthermore, the data obtainer 130 may obtain an average value of pieces of data corresponding to a frequency within a prescribed range. For example, the data obtainer 130 may obtain an average value of the pieces of data corresponding to a frequency of 90 MHZ to 110 MHZ. Furthermore, the data obtainer 130 may set respective ranges of preset frequencies. For example, when a preset frequency is 10 MHz and 200 MHz, the data obtainer 130 may obtain data corresponding to a frequency of 9 MHZ to 11 MHZ with respect to 10 MHz, and may obtain data corresponding to a frequency of 150 MHZ to 250 MHZ with respect to 200 MHz. The data obtainer 130 may obtain data corresponding to a frequency input by a user including the preset frequency from the extracted spectrum data. For example, if a frequency of 50 MHz is input by a user, the data obtainer 130 may obtain data corresponding to the frequency of 50 MHz.

Since every piece of measuring equipment may have a different resolution, if a variable, which is obtained via measuring equipment having a high resolution through the IAMB algorithm, is directly used when another equipment having a lower resolution is used, a model may not be properly operated. For example, it is impossible to apply a variable obtained through the IAMB algorithm with a spectrum obtained via measuring equipment having a resolution of 1 nm to measuring equipment having a resolution of 10 nm. Therefore, it is required to correct the variable obtained through the IAMB algorithm according to the resolution of the equipment. For example, a prescribed bandwidth value of a selected wavelength or an average of the bandwidth value may be used for correcting the variable.

The model obtainer 140 may obtain a biological information-measuring model by performing multiple linear regression (MLR) on obtained data. The model obtainer 140 may obtain a biological information-measuring model by performing MLR on the obtained average value.

The biological signal measurer 150 may measure a biological signal of a body part by using the biological information-measuring model. Furthermore, the biological signal measurer 150 may measure a biological signal of a body part, for example, a cholesterol value or blood sugar, by using the biological information-measuring model and data corresponding to the input frequency.

FIGS. 2 through 6 are exemplary views illustrating a method of measuring a biological signal according to an embodiment.

Figure 2:
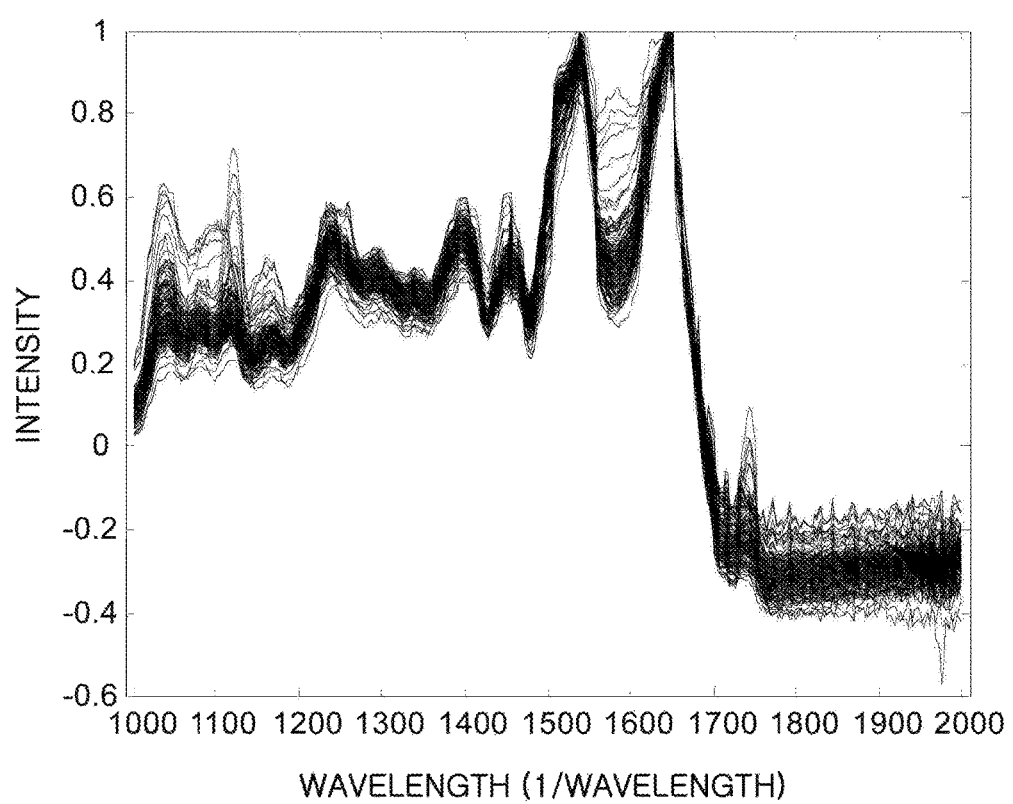
FIGS. 2, 3, 4, 5, and 6 are exemplary views illustrating a method of measuring a biological signal according to an exemplary embodiment
Figures 3, 4:
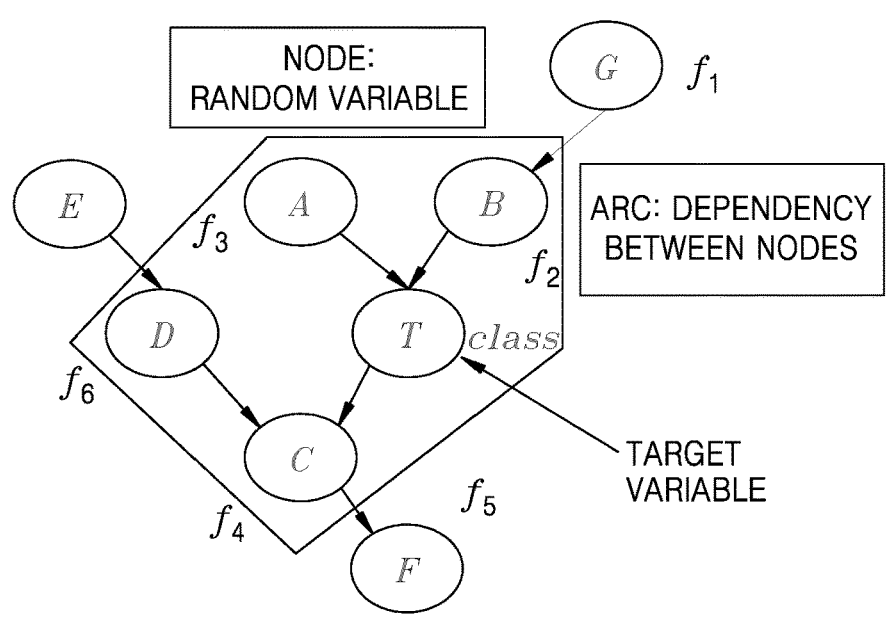

FIG. 2 is a graph of spectrum data extracted from an infrared signal which is irradiated toward a body part and is reflected therefrom. Infrared may include near infrared. Furthermore, the infrared may irradiate skin on the body part. A horizontal axis of the graph in FIG. 2 indicates a length of a spectrum wavelength, which is the same as the threshold of a frequency. Furthermore, a vertical axis of the graph indicates intensity of the spectrum wavelength. The spectrum may be obtained from a sample by spectroscopy. FIG. 3 is a view illustrating the spectrum data of FIG. 2, which is arranged in a matrix to be analyzed by the IAMB algorithm.

FIG. 4 is a view illustrating IAMB algorithm from among Markov Blanket searching algorithms. The biological signal measuring device 100 (of FIG. 1) selects a wavelength by using the IAMB algorithm from among Markov Blanket searching algorithms. The biological signal measuring device 100 verifies cross validity for optimal selection. The IAMB algorithm includes grow-and-shrink operations. Through a conditional independence test with a target node, the grow operation may repeat a successive adding operation of nodes having high relevance to the target node to a Markov Blanket (MB) group, until when the MB group does not change anymore. 'T' in FIG. 4 is a target variable. Referring to FIG. 4, a wavelength having the highest relevance to the target variable 'T' may be selected during the grow operation. The shrink operation reconfirms whether the nodes added during the grow operation are actual MBs. False positive nodes are removed through the conditional independence test, and remaining nodes become MBs. The remaining nodes may include a random variable.

Figures 5, 6:
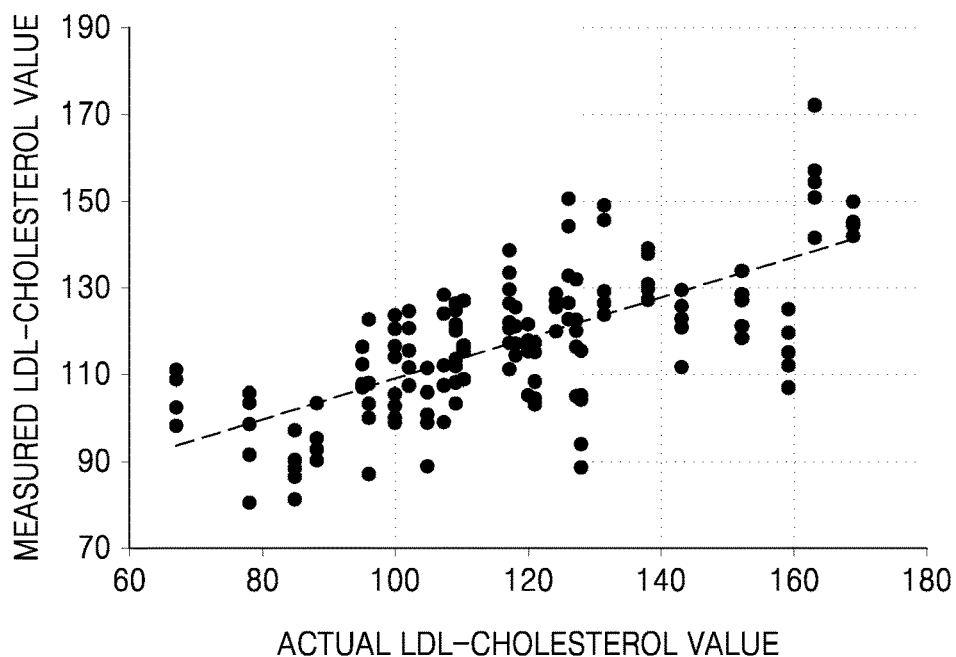

FIG. 5 is a view of a pseudo code with respect to a method of performing the IAMB algorithm. The IAMB algorithm includes grow-and-shrink operations. Lines 2-6 in FIG. 5 indicate grow operations. Through a conditional independence test with a target node, the first grow operation may repeat a successive adding operation of nodes most dependent on a target node (i.e., nodes having the highest relevance to a target node) to an MB group, until when the MB group does not change anymore. In the grow operation, that is, a first operation, nodes having a high probability of being an MB of a target node are preferentially added. Lines 7-9 in FIG. 5 indicate shrink operations. In the shrink operation, that is, a second operation, it is reconfirmed whether nodes added during the grow operation are actual MBs of a target node, and nodes judged as false positive nodes are removed from the MB group through the conditional independence test. Nodes remaining in the MB group after these operations become MBs with respect to a target node.

After a variable is selected through the IAMB algorithm, regression progresses based on the selected variable. An entry 1 in a first row of a matrix $[DAT_k]$ of FIG. 3 corresponds to an intercept of a regression coefficient. $[DAT_k]$ is an n*(k+1) matrix. A multiple regression model using a k selected spectrum intensity is defined according to Equation 1 below.

$$y=[DAT_k]\beta+\varepsilon \quad \text{[Equation 1]}$$

In Equation 1, y denotes a vector of an observation value (a biological signal) of a training sample, β denote regression coefficients. The regression coefficients β are obtained by using Equation 2 below.

$$\beta=[(DAT_k)'(DAT_k)]^{-1}*(DAT_k)'Y \quad \text{[Equation 2]}$$

After intensity data of a selected wavelength is formed in a matrix ($[DAT_k]$), a transpose matrix of the data is multiplied ($[DAT_k]'*[DAT_k]$), and an inverse matrix is obtained. Regression coefficients are obtained by multiplying $(DAT_k)$'Y by the intensity data.

Furthermore, with respect to an unknown sample (target) to be measured, spectrum intensity may be measured under the same condition as that of when the training sample is measured, and a measured value of the sample may be obtained as below. A measured value of a biological signal is denoted as [Ypred] by multiplying $[DAT_k]$ by [β].

FIG. 6 is a graph of a relationship between a spectrum and a low-density lipoprotein (LDL)-cholesterol value by applying a method of measuring a biological signal, according to an embodiment. Referring to FIG. 6, a correlation degree between an actual LDL-cholesterol value and a measured LDL-cholesterol value can be seen. For example, when measuring an LDL-cholesterol value by using a partial least-square (PLS) method, a correlation coefficient with an actual LDL-cholesterol value is 0.11. However, the correlation coefficient is 0.88, which is higher than above, when performing MLR on a wavelength selected through the IAMB algorithm.

Figure 7:
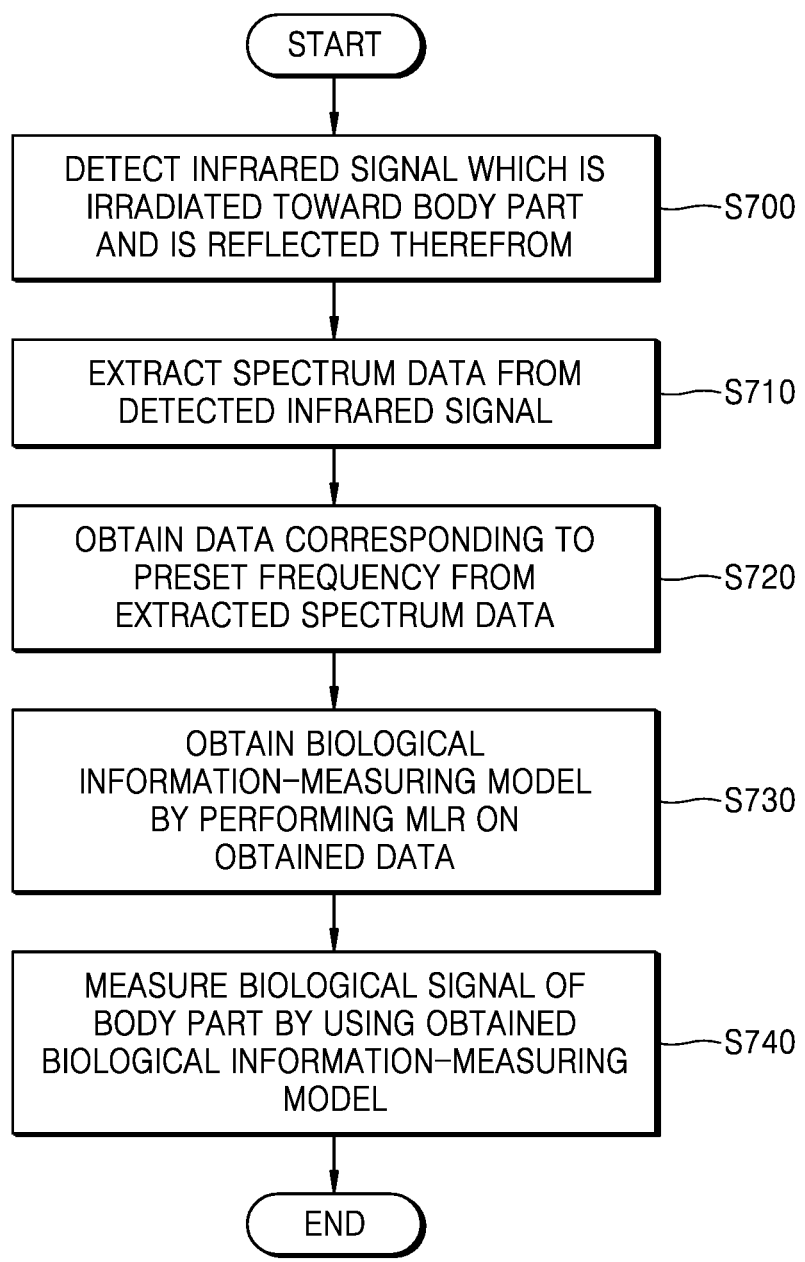
FIG. 7 is a flowchart of a method of measuring a biological signal according to an exemplary embodiment.

FIG. 7 is a flowchart of a method of measuring a biological signal according to an embodiment. Referring to FIG. 7, the biological signal measuring method includes operations that are time-sequentially processed in the device 100 of FIG. 1. Therefore, even if the descriptions are omitted below, the contents described above with respect to the device 100 of FIG. 1 may also be applied to the method of FIG. 7.

In operation S700, the device 100 may detect an infrared signal which is irradiated toward a body part and is reflected therefrom. Furthermore, the device 100 may also detect an infrared signal which is irradiated toward a body part and is scattered therefrom.

In operation S710, the device 100 may extract spectrum data from the detected infrared signal.

In operation S720, the device 100 may obtain data corresponding to a preset frequency from the extracted spectrum data.

In operation S730, the device 100 may obtain a biological information-measuring model by performing MLR on the obtained data.

In operation S740, the device 100 may measure a biological signal of a body part by using the obtained biological information-measuring model.

Figure 8:
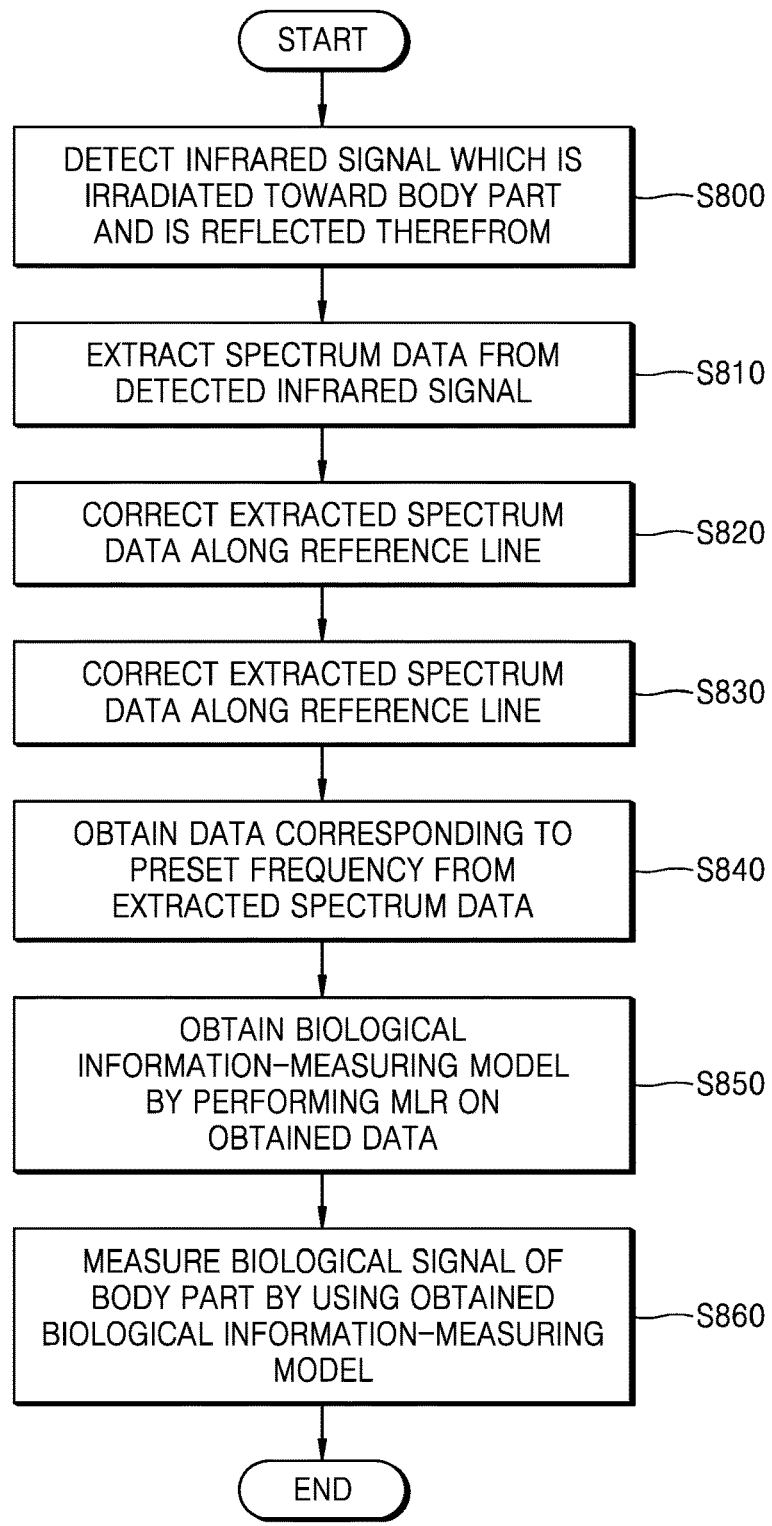
FIG. 8 is a flowchart of a method of measuring a biological signal according to another exemplary embodiment.

FIG. 8 is a flowchart of a method of measuring a biological signal according to another embodiment. Referring to FIG. 8, the biological signal measuring method includes operations that are time-sequentially processed in the device 100 of FIG. 1. Therefore, even if the descriptions are omitted below, the contents described above with respect to the device 100 of FIG. 1 may also be applied to the method of FIG. 8.

In operation S800, the device 100 may detect an infrared signal which is irradiated toward a body part and is reflected therefrom.

In operation S810, the device 100 may extract spectrum data from the detected infrared signal.

In operation S820, the device 100 may correct the extracted spectrum data along a reference line.

In operation S830, the device 100 may correct a basic value of the extracted spectrum data.

In operation S840, the device 100 may obtain data corresponding to a preset frequency from the extracted spectrum data.

In operation S850, the device 100 may obtain a biological information-measuring model by performing MLR on the obtained data.

In operation S860, the device 100 may measure a biological signal of a body part by using the obtained biological information-measuring model.

The device described herein may comprise a processor, a memory for storing program data and executing it, a permanent locker unit such as a disk drive, a communication port for handling communications with external devices, and user interface devices including a touch panel, keys, buttons, etc. When software modules or algorithms are involved, these software modules may be stored as program instructions or computer-readable codes executable on a processor on a computer-readable recording medium. Examples of the computer-readable recording medium include magnetic storage media (e.g., ROM, RAM, floppy disks, hard disks, etc.), and optical recording media (e.g., CD-ROMs, digital versatile disks (DVDs), etc.). The computer-readable recording medium can also be distributed over network-coupled computer systems so that the computer-readable code is stored and executed in a distributive manner. This media can be read by the computer, stored in the memory, and executed by the processor.

The present disclosure may be illustrated by functional block formations and various processing operations. Such functional blocks may be realized by a multiple number of hardware configurations performing particular functions and/or software configurations. For example, the present disclosure may adopt IC formations such as memory, processors, logic units and look-up tables, which can perform various functions by controlling more than one microprocessor or by other control systems. Similarly to formation elements being capable of being executable by software programming or software factors, the present disclosure may be realized by programming or scripting languages such as C, C++, Java and assembler, including various algorithms realized by a combination of data structures, processes, routines or other programming formations. Functional aspects may be realized by algorithms executed in more than one processor. Functional aspects may be realized by algorithms executed in more than one processor. In addition, the present disclosure may adopt related-art technology for electronic environment set-up, signal processing, and/or data processing, etc. Terms such as "mechanism", "element", "means" and "formation" may be widely used, and not limited to mechanical and physical formations. Terms above may include meanings of series of routines of software related to a processor, etc.

The particular implementations shown and described herein are illustrative examples and are not intended to otherwise limit the scope of the exemplary embodiments in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a", "an", and "the" and similar referents in the context of describing the exemplary embodiments (especially in the context of the following claims) are to be construed to cover both the singular and the plural. Furthermore, the recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The exemplary embodiments are not limited to the described order of the steps. The use of any and all examples, or exemplary language (e.g., "such as") provided herein, is intended merely to better illuminate the exemplary embodiments and does not pose a limitation on the scope of the exemplary embodiments unless otherwise claimed. Numerous modifications and adaptations will be readily apparent to one of ordinary skill in the art without departing from the spirit and scope of the exemplary embodiments.

It should be understood that the embodiments described herein should be considered in a descriptive sense only and not for purposes of limitation. Descriptions of the features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of measuring a biological variable, the method comprising:
   irradiating an infrared signal toward a body part;
   detecting an infrared signal of the irradiated infrared signal which is reflected from the body part;
   extracting spectrum data from the detected infrared signal;
   obtaining intensity data corresponding to a first frequency range and a second frequency range from the extracted spectrum data by using an Incremental Association Markov Blanket (IAMB) algorithm, wherein the first frequency range includes a first preset frequency, and the second frequency range includes a second preset frequency being higher than the first preset frequency;
   obtaining a biological information-measuring model by performing multiple linear regression (MLR) on the obtained intensity data; and
   measuring the biological variable of the body part by using the obtained biological information-measuring model.

2. The method of claim 1, wherein the obtaining the intensity data comprises obtaining an average value of intensity data corresponding to a plurality of preset frequency ranges, and the obtaining the biological information-measuring model comprises performing MLR on the obtained average value.

3. The method of claim 1, wherein the extracting the spectrum data comprises correcting the extracted spectrum data along a reference line.

4. The method of claim 1, wherein the extracting the spectrum data comprises correcting a value of the extracted spectrum data.

5. The method of claim 1, wherein the obtaining the intensity data comprises obtaining intensity data corresponding to a frequency input by a user.

6. The method of claim 5, wherein the measuring the biological variable of the body part comprises measuring the biological variable of the body part based on the intensity data corresponding to the frequency input by the user and the biological information-measuring model.

7. A device for measuring a biological signal, the device comprising:
an infrared detector, wherein an infrared signal is irradiated toward a body part by a device for irradiating the infrared signal, and the infrared detector is configured to detect an infrared signal of the irradiated infrared signal which is reflected from the body part; and
one or more processors configured to:
extract spectrum data from the detected infrared signal;
obtain intensity data corresponding to a first frequency range and a second frequency range from the extracted spectrum data by using an Incremental Association Markov Blanket (IAMB) algorithm, wherein the first frequency range includes a first preset frequency, and the second frequency range includes a second preset frequency being higher than the first preset frequency;
obtain a biological information-measuring model by performing multiple linear regression (MLR) on the obtained intensity data; and
measure a biological variable of the body part by using the obtained biological information-measuring model.

8. The device of claim 7, wherein the one or more processors are further configured to obtain an average value of intensity data corresponding to a plurality of preset frequency ranges, and obtain the biological information-measuring model by performing MLR on the obtained average value.

9. The device of claim 7, wherein the one or more processors are further configured to correct the extracted spectrum data along a reference line.

10. The device of claim 7, wherein the one or more processors are further configured to correct a value of the extracted spectrum data.

11. The device of claim 7, wherein the one or more processors are further configured to obtain intensity data corresponding to a frequency input by a user.

12. The device of claim 11, wherein the one or more processors are further configured to measure the biological variable of the body part based on the intensity data corresponding to the frequency input by the user and the biological information-measuring model.

13. A non-transitory computer-readable recording medium having recorded thereon a computer program for executing the method of claim 1.

14. A method of determining a biological variable, comprising:
irradiating an infrared signal toward a body part;
detecting an infrared signal of the irradiated infrared signal which is reflected from the body part;
extracting spectrum data from the detected infrared signal;
obtaining intensity data corresponding to a first frequency range and a second frequency range from the extracted spectrum data by using an Incremental Association Markov Blanket (IAMB) algorithm, wherein the first frequency range includes a first preset frequency and the second frequency range includes a second preset frequency being higher than the first preset frequency;
obtaining an observation vector comprising an observed value of the biological variable corresponding to the first frequency range and the second frequency range;
obtaining a biological information-measuring model by performing multiple linear regression (MLR) on the obtained intensity data and the observation vector; and
measuring the biological variable of the body part by using the obtained biological information-measuring model.

* * * * *